United States Patent
Apte et al.

(10) Patent No.: US 11,572,555 B2
(45) Date of Patent: Feb. 7, 2023

(54) METHOD AND SYSTEM FOR CRISPR-BASED LIBRARY PREPARATION AND SEQUENCING

(71) Applicant: PSOMAGEN, INC., Rockville, MD (US)

(72) Inventors: Zachary Apte, San Francisco, CA (US); Jessica Richman, San Francisco, CA (US); Daniel Almonacid, San Francisco, CA (US); Audrey Goddard, San Francisco, CA (US); Rodrigo Ortiz, San Francisco, CA (US); Sara Bird, San Francisco, CA (US); Eduardo Morales, San Francisco, CA (US)

(73) Assignee: Psomagen, Inc., Rockville, MD (US)

( * ) Notice: Subject to any disclaimer, the term of this patent is extended or adjusted under 35 U.S.C. 154(b) by 52 days.

(21) Appl. No.: 15/717,807

(22) Filed: Sep. 27, 2017

(65) Prior Publication Data

US 2018/0087051 A1    Mar. 29, 2018

Related U.S. Application Data

(60) Provisional application No. 62/400,401, filed on Sep. 27, 2016.

(51) Int. Cl.
*C12N 15/10* (2006.01)
(52) U.S. Cl.
CPC ..... *C12N 15/1082* (2013.01); *C12N 15/1089* (2013.01); *Y02A 90/10* (2018.01)
(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 7,323,305 | B2 | 1/2008 | Leamon et al. |
| 3,003,330 | A1 | 8/2011 | Heiner et al. |
| 2005/0124010 | A1 | 6/2005 | Short et al. |
| 2010/0105576 | A1 | 4/2010 | Jackson et al. |
| 2014/0357523 | A1 | 12/2014 | Zeiner et al. |
| 2015/0259728 | A1 | 9/2015 | Cutliffe et al. |
| 2016/0362748 | A1 | 12/2016 | Mongan et al. |
| 2017/0058339 | A1 | 3/2017 | Chee |

FOREIGN PATENT DOCUMENTS

| | | |
|---|---|---|
| WO | 20150113063 A1 | 7/2015 |
| WO | 2016065075 A1 | 4/2016 |
| WO | 2016/079731 A2 | 5/2016 |
| WO | 2016/100955 A2 | 6/2016 |

OTHER PUBLICATIONS

Kebschull et al. Nucleic Acids Research, 2015, vol. 43, No. 21.*
Woo et al Then and now: use of 16S rDNA gene sequencing for bacterial identification and discovery of novel bacteria in clinical microbiology laboratories Clin Microbiol Infect 2008; 14: 908-934.*

* cited by examiner

*Primary Examiner* — Joseph Woitach
(74) *Attorney, Agent, or Firm* — Morgan, Lewis & Bockius LLP

(57) ABSTRACT

Embodiments of a method and system for improved microbiome sequencing can include: generating guide RNA complexes for a set of targets corresponding to a set of taxa associated with the microorganism-related condition; processing the biological sample with the gRNA complexes to generate microorganism nucleic acid fragments comprising a set of end regions associated with the set of targets; ligating the set of end regions with a set of adapters sharing an adapter sequence; and amplifying the set of targets based on the ligated set of end regions and a set of primers sharing a primer sequence associated with the adapter sequence.

11 Claims, 4 Drawing Sheets

METHOD AND SYSTEM FOR CRISPR-BASED LIBRARY PREPARATION AND SEQUENCING

CROSS-REFERENCE TO RELATED APPLICATIONS

This application claims the benefit of U.S. Provisional Application Ser. No. 62/400,401, filed on 27 Sep. 2016, which is incorporated herein in its entirety by this reference.

TECHNICAL FIELD

This invention relates generally to the field of molecular diagnostics and more specifically to a new and useful method and system for CRISPR-based library preparation and sequencing in the field of molecular diagnostics.

BACKGROUND

Processes involving identification, amplification and analysis of nucleic acid targets within a sample can be used for sample characterization and/or diagnostic testing in research or clinical environments. Identification, detection, amplification, and analysis of multiple nucleic acid targets are thus particularly useful in characterizing multiple sample components and or enabling diagnostics associated with multiple targets (e.g., health condition biomarkers). Current methods and systems for multiplexed amplification, detection, sequencing, and/or analysis of multiple nucleic acid targets in a high throughput manner are, however, subject to limitations in terms of fragment assembly and sequence identification, especially in the context of highly polymorphic sequences.

Sequencing of multiple targets, in particular, is also typically limited by the number of reactions that can be performed within a single system (e.g., process chamber), downstream assembly, and interference factors associated with multiplexed reactions. Furthermore, current methods of multiplex sample processing are time consuming, labor intensive, and can be prohibitively expensive to implement.

As such, there is a need in the field of molecular diagnostics for a new and useful method and system for CRISPR-based library preparation and sequencing. This invention creates such a new and useful method and system.

DESCRIPTION OF THE EMBODIMENTS

The following description of the embodiments of the invention is not intended to limit the invention to these embodiments, but rather to enable any person skilled in the art to make and use this invention.

1. Overview.

Figure 1:
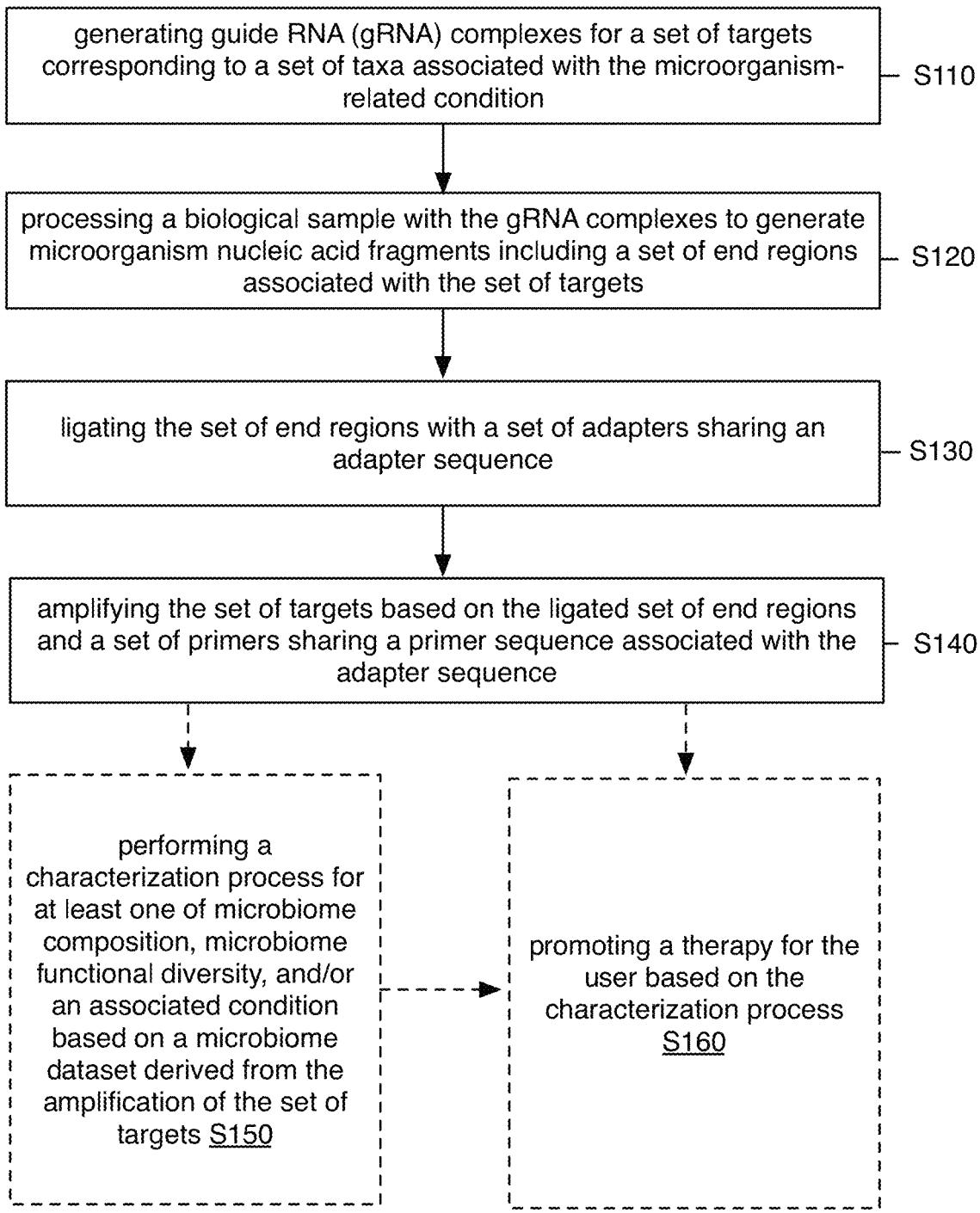
FIG. 1 is a flowchart schematic of an embodiment of a method for improved microbiome sequencing.
Figure 2:
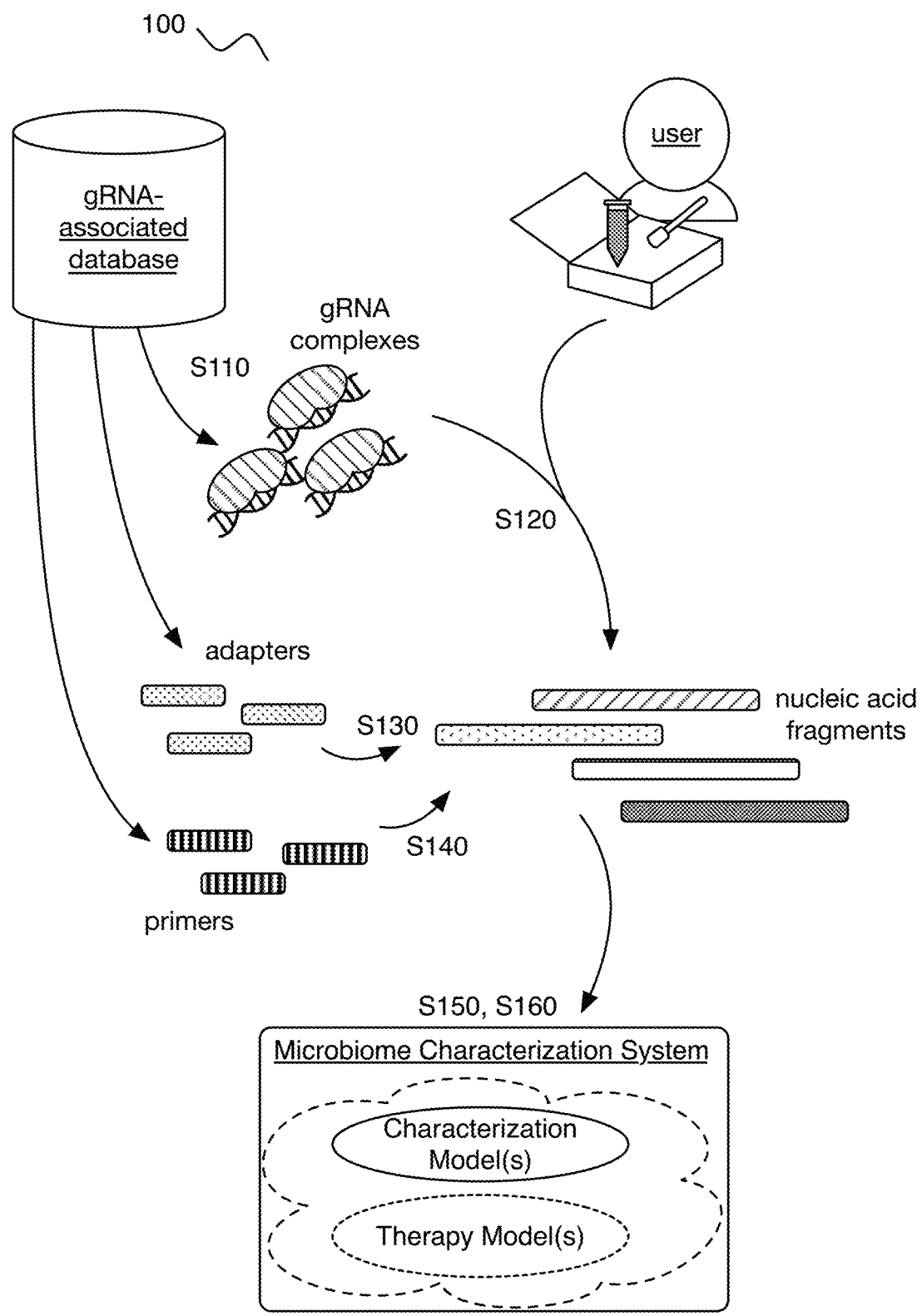
FIG. 2 is a schematic representation of an embodiment of a method for improved microbiome sequencing.
Figure 3:
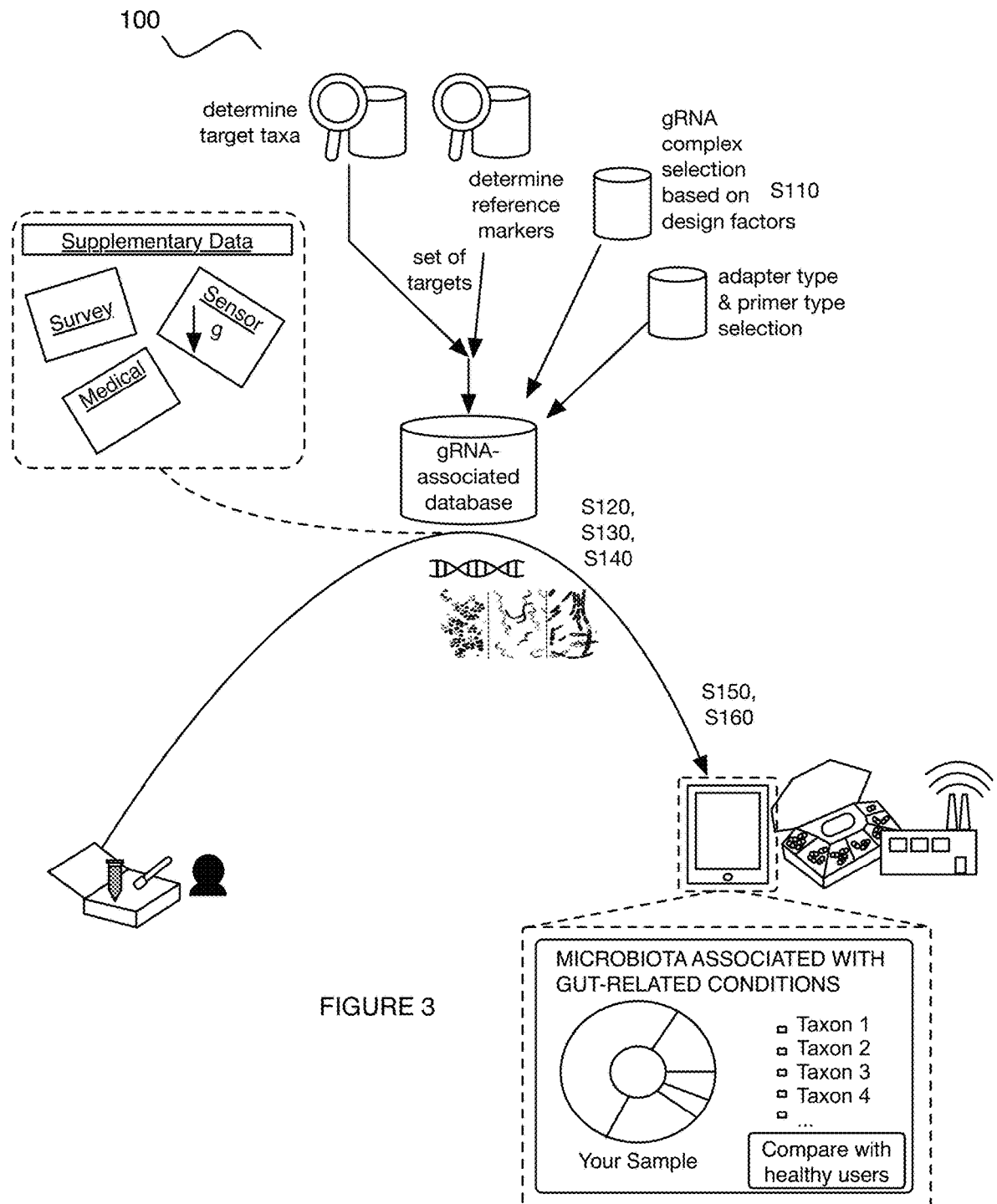
FIG. 3 is a schematic representation of an embodiment of a method for improved microbiome sequencing.

As shown in FIGS. 1-3, embodiments of a method 100 for improved microbiome sequencing can include: generating guide RNA (gRNA) complexes for a set of targets corresponding to a set of taxa associated with the microorganism-related condition S110; processing the biological sample with the gRNA complexes to generate microorganism nucleic acid fragments including a set of end regions (e.g., blunt end regions, sticky end regions, etc.) associated with the set of targets S120; ligating the set of end regions with a set of adapters sharing an adapter sequence S130; and amplifying the set of targets based on the ligated set of end regions and a set of primers sharing a primer sequence associated with the adapter sequence S140. Additionally or alternatively, the method 100 can include: performing a characterization process for at least one of microbiome composition, microbiome functional diversity, and/or an associated condition based on a microbiome dataset (e.g., microbiome composition diversity dataset; microbiome functional diversity data; microbiome pharmacogenomics dataset, etc.) derived from the amplification of the set of targets (e.g., generating the microbiome dataset through sequencing the amplified targets; etc.) S150; promoting a therapy for the user based on the characterization process S160; and/or any other suitable processes.

Embodiments of the method 100 and/or system 200 can function to provide improved sample processing protocols for improving sequencing associated with microorganisms. For example, the technology can remove/mitigate interference issues associated with multiplexed primer processes, which can significantly reduces amplification biases associated with amplicon sequencing methods involving hybridization of a primer with a target sequence and several cycles of amplification. In a specific example, the method 100 implements gRNAs for generation of gRNA complexes (e.g., protein-RNA complexes) in a manner that can reduce or eliminate amplification interference issues associated with primers, due to the binding energy characteristics of protein-RNA complexes. The method 100 can thus provide an efficient technique for target amplification in a way that improves upon current amplification based techniques (e.g., techniques involving Nextera kits). In another specific example, the method 100 can be used to amplify and sequence highly polymorphic sequences (e.g., 16S rRNA sequences, 18S rRNA sequences, ITS sequences, etc.) or any other suitable sequence. Thus, the method 100 can be used for microbiome-associated characterization, diagnostic applications involving nucleic acid analysis, and/or any other suitable downstream application requiring sequence amplification and analysis.

In examples, the method 100 and/or system 200 can generate and/or promote characterizations and/or therapies for a condition and/or panel of conditions, which can include one or more of: symptoms, causes, diseases, disorders, microbiome pharmacogenomics profiles (e.g., describing resistance and/or susceptibility to antibiotics) and/or any other suitable aspects associated with the panel of conditions. Conditions can include one or more of: gut-related conditions; psychiatric and behavioral conditions (e.g., a psychological disorder; depression; psychosis; etc.); communication-related conditions (e.g., expressive language disorder; stuttering; phonological disorder; autism disorder; voice conditions; hearing conditions; eye conditions; etc.); sleep-related conditions (e.g., insomnia, sleep apnea; etc.); a cardiovascular-related condition (e.g., coronary artery disease; high blood pressure; etc.); metabolic-related conditions (e.g., diabetes, etc.), rheumatoid-related conditions (e.g., arthritis, etc.); weight-related conditions (e.g., obesity, etc.); pain-related conditions; endocrine-related conditions; genetic-related conditions; chronic disease; and/or any other suitable type of conditions. Gut-related conditions can include any one or more of: diarrhea, irritable bowel syndrome (IBS), inflammatory bowel disease (IBD), Crohn's Disease, ulcerative colitis, constipation, abdominal tenderness, bloating, flatulence, obesity, type II diabetes, prediabetes, kidney stones, cardiovascular health, and anxiety, other suitable gut conditions, and/or any conditions described in U.S. application Ser. No. 15/707,907 filed 18 Sep. 2017, which is herein incorporated in its entirety by this reference.

In variations, Blocks of the method 100 can be repeatedly performed in any suitable order to enable refining of an gRNA-associated database (e.g., through identification and selection of updated gRNA sequences, adapter sequences, primer sequences, etc.), refining of the characterization process (e.g., through updating characterization models, therapy models, and/or other suitable models based on microbiome datasets derived from sample processing according to portions of the method 100; through increasing the number of conditions that can be characterized using a single biological sample; etc.), the therapy process (e.g., through monitoring and modulating microbiome composition with therapies over time based on microbiome-associated characterizations for users over time, where the therapies can be selected based on characterization results possessing sensitivity, specificity, precision, and negative predictive value; etc.), and/or other suitable processes.

Additionally or alternatively, data described herein (e.g., design-related data for gRNAs, adapters, primers; microorganism datasets; microbiome features; microbiome-related characterizations such as panel characterizations and/or probiotics-related characterizations; population-level data; user-level data; treatment-related data; etc.) can be associated with any suitable temporal indicators (e.g., seconds, minutes, hours, days, weeks, etc.; temporal indicators indicating when the data was collected, determined and/or otherwise processed; temporal indicators providing context to content described by the data, such as temporal indicators indicating a state of a panel of conditions at the time at which the biological sample was collected; etc.) and/or change in temporal indicators (e.g., microbiome features over time; microbiome composition diversity, functional diversity, and/or other suitable aspects over time; change in data; data patterns; data trends; data extrapolation and/or other prediction; etc.).

Figure 4:
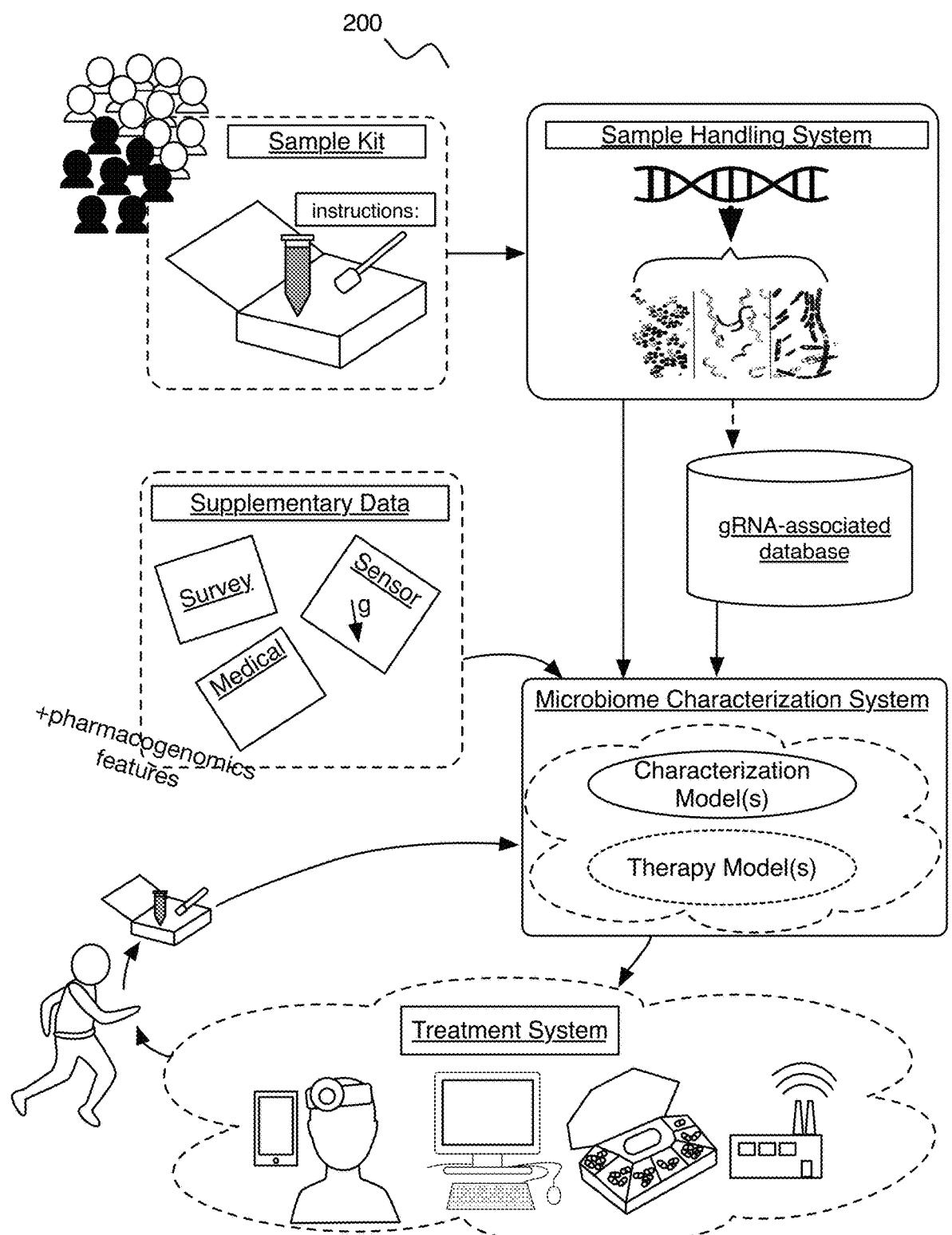
FIG. 4 is a schematic representation of an embodiment of a system for improved microbiome sequencing.

One or more instances of the method 100 and/or processes described herein can be performed asynchronously (e.g., sequentially), concurrently (e.g., in parallel; targeting, amplifying, and/or otherwise performing sequencing-related processes for a plurality of microorganism-related targets; multiplexing to enable processing of multiple biological samples in parallel, such as for a plurality of users; computationally characterizing different microbiome features and/or microorganism-related conditions concurrently on different threads for parallel computing to improve system processing ability; etc.), in temporal relation to a trigger event, and/or in any other suitable order at any suitable time and frequency by and/or using one or more instances of the system (e.g., including a sample handling network, a panel characterization system, a therapy system, sample kits, etc.), elements, and/or entities described herein. As shown in FIG. 4, portions of the method 100 can be implemented at least in part at a computing system, where the computing system can be implemented in one or more of a computer, a workstation associated with an automated laboratory system, a semi-automated laboratory system, a remote server, a cloud-based computing system, a computing module of a mobile computing device, and any other suitable computing module. In variations, the method 100 can be implemented by at least components described in U.S. application Ser. No. 14/593,424 entitled "Method and System for Microbiome Analysis" and filed on 9 Jan. 2015, which is herein incorporated in its entirety by this reference, and/or by any suitable components of a system 200.

As shown in FIG. 4, embodiments of the method 100 can be implemented by at least embodiments of a system 200 for improved microbiome sequencing, where the system 200 can include a gRNA-associated database (including gRNA sequence data; adapter sequence data; target taxonomic group sequence data; sequences selected based on design factors; etc.); a sample handling system operable to process biological samples with gRNA complexes, adapters, primers, and/or other suitable molecules for facilitating microbiome dataset generation; a microbiome characterization system operable to determine characterizations for one or more users for one or more microorganism-related conditions; a treatment system operable to promote therapies; and/or any other suitable components. However, the method 100 and system 200 can be performed in any suitable manner.

2. Benefits.

Specific examples of the method 100 and/or system 200 can confer technologically-rooted solutions to challenges arising from conventional approaches. First, the technology can confer improvements in reducing amplification biases; reducing primer interference effects; performing sequencing associated with a plurality of microorganism targets; sample processing efficiency; computational processing speed; microbiome-related characterization accuracy; microbiome-related therapy determination and promotion, and/or other suitable aspects associated with the technical fields of microbiome sequencing and/or related sample preparation.

Second, the technology can transform entities (e.g., users, biological samples, treatment systems including medical devices, etc.) into different states or things. For example, the technology can transform a biological sample into a microbiome-related characterization for a microorganism-associated condition through improved sample processing operations for improved sequencing. In another example, the technology can identify therapies to promote to a patient to modify a microbiome composition, microbiome functional diversity, a microbiome pharmacogenomics profile and/or other microbiome-related aspects to prevent and/or ameliorate one or more microorganism-related conditions, thereby transforming the microbiome and/or health of the patient. In another example, the technology can transform a biological sample (e.g., through processing with gRNA complexes, adapters, primers, amplification operations, sequencing operations, etc.) received by patients into microbiome datasets, which can be correlated with microorganism-related conditions. In another example, the technology can control treatment systems to promote therapies (e.g., by generating control instructions for the treatment system to execute), thereby transforming the treatment system.

Third, the technology can amount to an inventive distribution of functionality across a network including a gRNA-associated database, a sample handling system, a microbiome characterization system, and a plurality of users, where the sample handling system can handle substantially concurrent processing of biological samples for a plurality of microorganism targets, which can be leveraged in generating personalized characterizations and/or therapies (e.g., customized to the user's microbiome such as in relation to the user's dietary behavior, probiotics-associated behavior, medical history, demographics, other behaviors, preferences, etc.) for microorganism-related conditions.

Fourth, the technology can leverage specialized sample processing devices (e.g., next generation sequencing devices; CRISPR-related devices; panel characterization systems; treatment systems; etc.) in performing portions of the method 100. The technology can, however, provide any other suitable benefit(s) in the context of using non-generalized systems for improved sequencing.

3.1 Generating gRNA Complexes.

Block Silo recites: generating gRNA complexes for a set of targets corresponding to a set of taxa associated with the microorganism-related condition, which can function to guide gRNAs and/or associated biomolecules (e.g., proteins such as endonucleases, etc.) to facilitate processing activity for microorganism nucleic acids in collected biological samples (e.g., activity associated with blunt end formation and ligation, in relation to sequence positions of the set of targets, etc.). In particular, the gRNAs generated in Block Silo and used in subsequent steps of the method 100 can reduce/eliminate amplification interference issues associated with primers, due to the binding energy characteristics of protein-RNA complexes generated using the gRNAs. The set of gRNAs can further be used to facilitate targeting a desired/specific region of a genome and amplification of sequences from 150-500 base pairs (bps), preferably on the order of 300 base pairs (bps), such as 16S rRNA gene regions, without requiring downstream assembly steps. Additionally or alternatively, targets can be of any suitable size (e.g., any suitable number of base pairs) and can include and/or otherwise be associated with any suitable functional, structural, evolutionary, and/or other suitable characteristics. Targets preferably include target nucleic acid sequences (e.g., RNA sequences, DNA sequences, biomarker sequences indicative of different microorganism-related taxa; etc.), but any suitable guide complexes (e.g., gRNA complexes, guide non-RNA complexes, etc.) can be used to target any suitable microorganism-related targets (e.g., 16S rRNA targets, 18S rRNA targets, etc.) including any one or more of: protein coding genes (e.g., serum proteins, antibodies, peptides, etc.), LPS pattern as biomarker, microorganism biomarkers, genetic predisposition biomarkers, diagnostic biomarkers, prognostic biomarkers, predictive biomarkers, other molecular biomarkers, gene expression markers, imaging biomarkers, and/or other suitable markers.

As such, Block Silo (e.g., in combination with Block S130, etc.) can provide an improvement and/or alternative to fragmentation, amplification, sequencing and/or assembly protocols, such as in a manner that allows for simultaneous amplification of multiple targets in a reaction chamber without using multiplexed primers (e.g., multiple sets of primers with multiple different primer sequences complementary to different target sequences, etc.) that have a tendency to self adhere (dimerize), interfere with each other, and/or otherwise hinder amplification. As such, the method 100 described herein can obviate the need for multiplexed primers in relation to amplification of multiple targets in the same solution.

In Block S110, generating a set of gRNAs preferably implements an algorithm that selects gRNA sequences that have little-to-no tendency to form secondary structures and takes into account tendencies of candidate gRNAs to self-bind. The gRNA design and selection algorithm can thus rank candidate gRNA sequences based upon the set of genomic targets desired for amplification, based upon a set of gRNA design factors, based upon minimizing off-target activity/maximizing on-target activity (e.g., with analysis and selection of identification of potential protospacer sequences around target sites), and/or based upon any other suitable design factor. For example, Block Silo can include ranking gRNA sequences based upon a set of gRNA design factors for optimizing on-target activity. However, gRNA design factors and/or any other suitable design factors (e.g., for targets, adapters, primers, conditions, etc.) can be optimized for any suitable target parameters (e.g., accuracy; bias minimization; interference minimization; efficiency; speed; processing power; cost; etc.).

In variations, the set of gRNA design factors for selection of the set of gRNAs can include one or more of: a folding energy factor (e.g., associated with tendency to form secondary structures); a hybridization factor (e.g., associated with tendency to interact/interfere with other gRNAs in the mix); a GC content factor; a nucleotide run factor; a first binding energy factor (e.g., associated with a first subset of base pairs); a second binding energy factor (e.g., associated with a second subset of base pairs, if criteria associated with the first binding energy factor is satisfied); a GC clamp factor; and any other suitable factor. In variations, the algorithm for selection/generation of the set of gRNAs can be adapted from and/or analogous to method for multiplex primer design described in U.S. application Ser. No. 15/240,919 titled "Method and System for Multiplex Primer Design" and filed on 18 Aug. 2016, which is herein incorporated in its entirety by this reference.

In a specific example, the gRNA generation algorithm can implement criteria associated with a folding energy factor, a hybridization factor; a GC content factor; a nucleotide runs factor; a first binding energy factor (e.g., associated with the first 13 bps of a gRNA); a second binding energy factor (e.g., associated with a remainder of 7 bps, if criteria associated with the first binding energy factor is satisfied).

The set of gRNAs can be designed to target positions (e.g., positions associated with 16S rRNA gene regions, such as for a set of targets associated with 16S rRNA regions; positions associated with 18S rRNA gene regions; positions associated with ITS regions; etc.) associated with nucleic acid sequences of the same organism and/or associated with different organisms. Block S110 can be used to generate a single gRNA, a pair of gRNAs, and/or can be used to generate more than two gRNAs (e.g., 16S rRNA and 18S rRNA gRNAs) to be used to facilitate subsequent targeting, cutting, ligating, amplification processes, and/or any other suitable processes associated with sequencing. Additionally or alternatively, the set of gRNAs complexes can include any suitable number and types (e.g., different sequences) of gRNAs gRNA complexes preferably include gRNAs and one or more proteins of one or more protein types including any of: endonucleases (e.g., for generating end regions associated with targets), and/or other suitable protein types. Specific examples of proteins can include SpyCas9 (e.g., for generating blunt ends), other CRISPR-associated proteins (e.g., types including cas, cse, csy, csn, csd, cst, csh, csa, csm, cmr, cpf, etc.), Cpf1 (e.g., with different PAM sites for additional cut site options; for generation of an overhang for presenting different ligation strategies; requiring only a single RNA guide; etc.), and/or any other suitable types of proteins. For example, spCas9 enzyme can be complexed with gRNAs targeting the 16S region of bacteria. Additionally or alternatively, Block Silo can include generating guide non-RNA complexes excluding gRNAs, where the complexes can include any suitable types of molecules described herein. In variations, guide non-RNA complexes can be generated and/or applied in any manner analogous to processes (e.g., in relation to processes associated with gRNA complexes; in relation to portions of the method 100, etc.) described herein (e.g., such as in relation to end region generation, ligation, and amplification described herein), and/or can be generated and/or applied in any suitable manner. Block Silo can, however, be implemented in any other suitable manner.

3.2 Processing Samples with gRNA Complexes.

Block S120 recites: processing the biological sample with the gRNA complexes to generate microorganism nucleic acid fragments including a set of end regions (e.g., blunt end regions, sticky end regions, etc.) associated with the set of targets. Block S120 can function to use the set of gRNAs and an appropriate endonuclease to cut target sequences at the appropriate positions (e.g., protospacer positions) in a manner that produces (e.g., unilateral) end regions for subsequent processing (e.g., for ligation of adapters in Block S130, etc.). The processes used in Block S120 can thus use endonucleases (and/or other suitable proteins and/or processes) that produce blunt ends with high efficiency, or can additionally or alternatively use endonucleases that produce cohesive/sticky ends (e.g., overhangs), such as, for example, in combination with a treatment that converts sticky ends to blunt ends. In a variation, restriction endonucleases implemented in Block S120 are preferably RNA-guided nucleases. Additionally or alternatively, endonucleases and/or other suitable molecules can be guided to targets through any suitable mechanism. The restriction endonucleases can additionally or alternatively be palindromic, shifted cleavage, combined restriction and modification, or heterodimer type. However, generating end regions can be performed with any suitable complexes (e.g., guide non-RNA complexes), gRNAs, transcription processes (e.g., transcribing RNA from DNA), etc.), other proteins, and/or other suitable components.

Block S120 preferably uses a Cas9 restriction endonuclease that produces blunt ends associated with the gRNA target sites in a high efficiency manner. However, in relation to end region formation, Block S120 can additionally or alternatively use other RNA-guided restriction endonucleases and/or other suitable endonucleases for generating end regions (e.g., with high efficiency, etc.).

In relation to mitigating effects of sticky ends, Block S120 can include processing steps for blunting of sticky ends (e.g., at the 3' end, at the 5' end, at both ends, etc.) produced using the endonuclease(s). In one such variation, Block S120 can implement a T4 DNA polymerase treatment with buffer (i.e., 50 mM NaCl, 10 mM Tris-HCl, 10 mM $MgCl_2$, 100 µg/mL bovine serum albumin at pH 7.9) that blunts 3' overhangs. In other variations, Block S120 can implement one or more of: a DNA polymerase I Large (Klenow) Fragment fill-in protocol for blunting; a Mung Bean Nuclease for blunting; a Takara protocol for blunting; and/or any other suitable blunting protocol using appropriate polymerases or other materials. Additionally or alternatively, the method 100 can include implementation of adapted TA-cloning protocols to mitigate effects of low blunting efficiency.

In an example, the method 100 can include generating ribonucleoprotein complexes including CRISPR-associated proteins (e.g., SpyCas9) and gRNAs; processing the ribonucleoprotein complexes with a set of targets (e.g., target DNA, bacterial, viral, genomic, etc.) from a biological sample. In another example, a biological sample can be processed with molecules from transcribing RNA from DNA templates in generating end regions. However, biological samples including a set of targets can be processed in any suitable manner using any suitable gRNAs, gRNA complexes, other suitable complexes, ad/or other suitable molecules generated through any suitable processes.

Additionally or alternatively, in relation to processing with the set of gRNAs and the endonuclease(s), Block S120 can implement one or more of: viral delivery methods with one or more vectors (e.g., with AAV delivery of endonucleases); plasmid delivery methods, gesicle delivery methods, vesicle delivery methods, RNA delivery methods; and any other suitable delivery or transfection methods, including mixing and adding components. Additionally or alternatively any suitable in vitro and/or in vivo delivery approaches can be employed. However, processing the biological sample with gRNA complexes and/or any other suitable biomolecules can be performed in any suitable manner.

3.3 Ligating End Regions.

Block S130 recites: ligating the set of end regions with a set of adapters sharing an adapter sequence. Block S130 can function to use ligation techniques in ligating adapters (e.g., sharing an adapter sequence; including any number of subsets of adapters sharing any suitable number of adapter sequences; a single adapter; multiple adapters; etc.) at end regions (e.g., blunt end regions; sticky end regions; etc.), such as those generated in Block S120. For example, the method 100 can include processing a biological sample with gRNA complexes including endonucleases for generating microorganism nucleic acid fragments including a set of end regions (e.g., blunt end regions; sticky end regions; etc.) associated with the set of targets; and ligating the end regions with a set of adapters (e.g., sharing an adapter sequence; etc.). Additionally or alternatively, Block S130 can function to facilitate next-generation sequencing of the set of targets. For example, Block S130 can include selecting and applying adapters using adapter sequences tailored to sequencing systems (e.g., next generation sequencing systems, etc.); using adapter sequences complementary to primers tailored for sequencing systems; and/or other suitable processes. In another example, Block S130 can include applying adapters configured to facilitate direct sequencing (e.g., without amplification; with minimal amplification; through direct feeding into MinION systems, Illumina systems, etc.). In a specific example, Block S130 can include ligating dA, dT, dG, or dC tails to be used as complementary to primers tailored for preparing sequencing libraries. Additionally or alternatively, any suitable approaches can be applied using specifically selected adapters for facilitating direct sequencing. However, Block S130 can be applied in any suitable manner for enabling improved sequencing.

As such, the adapter type (e.g., adapter sequence) used (or limited number of adapter types) can enable the use of a single primer type (or a limited number of non-interfering primer types) in subsequent amplification steps, such as in a manner that can eliminate primer interference associated with multiplex primer use. In a specific example, all target sequences that have undergone the blunting process of Block S120 can undergo ligation with adapters sharing the same adapter sequence, and can be subsequently amplified with primers sharing the same primer sequence, which can thereby significantly reduce amplification bias effects and eliminating primer interference effects.

In a specific example demonstrating this benefit, a reduced number of cuts of the amplicons of interest and amplification using a single primer type can significantly reduce amplification bias, such as in comparison to standard methods of fragmentation, tagging, and amplification using a large plurality of primer types. In particular the method 100 described herein can significantly reduce the number of thermocycling iterations performed (where each iteration has a bias effect), as described in more detail in relation to Block S140 below.

The adapter type used in Block S130 is preferably platform specific (e.g., for Illumina™ platforms), and in specific examples, can include adapter components appropriate for one or more of: a HiSeq platform, a NextSeq platform, and/or a MiSeq platform. In alternative examples, the adapter can include adapter components appropriate for one of: a PacBio platform, a MinION platform, an Oxford Nanopore platform, a Roche 454 Life Sciences platform, a Life Technologies SOLiD platform, and any other suitable platform. Still alternatively, the adapter can include platform-nonspecific adapter components.

In a specific example, the adapter can include one or more of the following components: a forward index sequence (e.g., corresponding to an Illumina forward index for MiSeq/NextSeq/HiSeq platforms), or a reverse index sequence (e.g., corresponding to an Illumina reverse index for MiSeq/NextSeq/HiSeq platforms), a forward barcode sequence or a reverse barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, a sequence for targeting a specific target region, and any other suitable adapter component. In variations, Block S130 and/or any other portions of the method 100 can include any approaches described in and/or analogous to U.S. Provisional App. No. 62/522,293 filed 20 Jun. 2017, which is herein incorporated in its entirety by this reference.

Block S130 preferably includes implementing an end region ligation protocol (e.g., a blunt end region ligation protocol; a sticky end region ligation protocol; etc.). In variations, the end region ligation protocol can be a restriction cloning protocol. In a first specific example, the ligation protocol can implement a T3 DNA ligase (e.g., bacteriophage T3 DNA ligase) with appropriate buffer materials. In other examples, the ligation protocol can implement any other suitable ligase(s) and/or ligation protocol steps to ligate adaptor components at end regions (e.g., generated in Block S120).

Additionally or alternatively, Block S130 can implement ligation operations (e.g., for improving ligation efficiency; for improving ligation specificity; etc.), including one or more of: increasing concentrations of inserts and/or ligases; performing ligation reactions in multiple steps (in a manner that reduces generation of concatemers); using longer incubation times; using reaction temperatures that are between the best temperature for DNA ligase activity and melting temperatures; dephosphorylating the vectors used; phosphorylating inserts used; reducing ATP concentration; using a polyethylene glycol (PEG)-rich ligation mixture; using lower concentration of monovalent cations in buffers; and/or any other suitable protocol step. Additionally or alternatively, ligation operations can include ligation associated with Cpf1 (e.g., with different PAM sites; requiring a single gRNA); and/or any other suitable ligation operations associated with any suitable endonucleases, adapters, proteins, and/or other suitable molecules.

However, ligating end regions with one or more adapters can be performed in any suitable manner.

3.4 Amplifying Targets.

Block S140 recites: amplifying the set of targets based on the ligated set of end regions and a set of primers sharing a primer sequence (e.g., through processing the ligated set of end regions with the set of primers, etc.) associated with the adapter sequence. Block S140 can function to amplify the set of targets (e.g., amplifying nucleic acid fragments including the set of targets; etc.) for subsequent sequencing and/or analysis (e.g., to characterize microbiome aspects of biological samples; to promote therapies based on microbiome-associated characterizations; etc.). For example, Block S140 can include performing, with a bridge amplification substrate of a next generation sequencing platform, multiplex amplification based on the set of primers and the set of adapters, and generating the microbiome dataset (e.g., microorganism sequence dataset, etc.), such as at a computing system operable to communicate with the next generation sequencing platform.

Block S140 preferably includes applying amplification operations with a single primer type associated with an adapter type used in Block S130 (e.g., applying a set of primers sharing a primer sequence associated with an adapter sequence shared by the set of adapters used, which can facilitate substantially simultaneous sequencing of a plurality of targets; etc.). As such, Block S140 can involve amplification in a manner that reduces or entirely eliminates primer interference factors (e.g., self-dimer formation, primer-dimer formation), and can reduce amplification bias. In a specific example, Block S140 can include amplifying a set of targets based on a set of primers consisting of primers sharing a primer sequence (e.g., exclusively using primers sharing a same primer sequence, etc.), in order to reduce amplification biases. Additionally or alternatively, the set of primers used in Block S140 can include any suitable number of subsets of primers sharing any suitable number of sequences. Thus, the primer/primer set can be selected to prevent or minimize amplification bias effects, and/or configured to amplify nucleic acid regions/sequences (e.g., of a 16S rRNA gene region, a 18S rRNA gene region, a ITS region, etc.) that can be informative taxonomically, phylogenetically, for diagnostics, and/or for any other suitable purpose.

In Block S140, amplifying can include one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and/or any other suitable amplification technique.

Due to the sample processing aspects of Blocks S110-S130, Block S140 can include amplification steps with a reduced number of thermocycling cycles (e.g., 10 or under, 20 or under, under 30, etc.), such as in a manner that maintains original proportions of amplicons (i.e., in relation to the original proportion of targets in a sample prior to amplification). In a specific example, with a reduced number of thermocycling cycles and a single primer/primer set for amplification, amplification biases can be significantly reduced, such that bias can be attributed solely to the gRNA RNAs used, rather than exponentially growing with each thermocycling cycle. However, any other suitable number of thermocycling cycles can be used in other variations of Block S140.

In specific examples, in the amplification of the targets processed with adapters, the primer/primer set (e.g., the primer type or types, etc.) used is preferably designed to universally amplify all of the targets in the sample, due to the single adapter type (or limited number of adapter types) used in ligation processes of Block S130. Primer types include universal primer types (e.g., where primer/primer sets can include universal primers). Additionally or alternatively, the primer/primer sets used in variations of Block S140 can additionally or alternatively include incorporated barcode sequences specific to each of the limited number of adapters. Additionally or alternatively, the primer/primer sets used in Block S140 can include degenerate primers. Additionally or alternatively, Block S140 can implement any other step configured to facilitate processing, amplification, and steps subsequent to amplification, some embodiments, variations, and examples of which are described in as described in U.S. application Ser. No. 15/097,862 entitled "Method and System for Microbiome-Derived Diagnostics and Therapeutics . . . " and filed on 13 Apr. 2016.

3.5 Performing a Characterization Process.

The method 100 can additionally or alternatively include Block S150, which recites: performing a characterization process (e.g., generating characterizations, etc.) for at least one of microbiome composition, microbiome functional diversity, and/or an associated condition based on a microbiome dataset (e.g., microbiome composition diversity dataset; microbiome functional diversity data; microbiome pharmacogenomics dataset, etc.) derived from the amplification of the set of targets (e.g., generating the microbiome dataset through sequencing the amplified targets; etc.). Block S150 can function to generate microbiome datasets and/or apply the microbiome datasets for generating microbiome-associated characterizations for a user. Performing a characterization process and/or any other associated processes (e.g., collecting biological samples; collecting supplementary datasets; extracting microbiome features; generating microbiome datasets; etc.) can be performed in any manner analogous to that described in U.S. application Ser. No. 15/707,907 filed 18 Sep. 2017, which is herein incorporated in its entirety by this reference.

Block S150 preferably includes generating one or more microbiome datasets, which can include one or more of: microorganism sequence datasets, microbiome composition diversity datasets (e.g., indicative of microbiome composition; extracted from microorganism sequence datasets; datasets from which microbiome composition diversity features can be extracted; etc.), microbiome functional diversity datasets (e.g., indicative of microbiome functional diversity; extracted from microorganism sequence datasets; datasets from which microbiome functional diversity features can be extracted; etc.), and/or any other suitable microbiome-associated datasets. For example, Block S150 can include: generating a microorganism sequence dataset (e.g., including microorganism sequences derived from sequencing the amplified set of targets generated in Block S140; including results from comparisons between user microorganism sequences and reference microorganism sequences, such as those correlated with microorganism-related conditions; etc.) for the user; and determining a microbiome-associated characterization for the user for the microorganism-related condition based on the microorganism sequence dataset, where the microbiome-associated characterization is configured to facilitate modification of the microbiome of the user in improving a state of the microorganism-related condition (e.g., through informing the user and/or an associated care provider of microbiome characteristics of the user and/or corresponding conditions; where the user can leverage the information to improve microbiome composition and/or functional diversity, such as through consumable therapies; etc.). Generating microbiome datasets is preferably based on sequenced set of targets (e.g., sequenced based on the amplified set of targets in Block S140, etc.). Block S150 can include performing sequencing (e.g., next generation sequencing with a next generation sequencing system; sequencing with any suitable types of sequencing systems; etc.) of the set of targets based on the ligated end regions (e.g., based on products generated from processing with the set of primers sharing a primer sequence associated with the adapter sequence; etc.). For example, However, performing sequencing operations and/or generating microbiome datasets can be performed in any suitable manner.

Block S150 preferably includes determining one or more microbiome-associated characterizations for one or more microorganism-related conditions (e.g., for characterizing a user; a subgroup of users; a population of users; etc.). In a specific example, Block S150 can include determining a microbiome-associated characterizations for a set of taxa corresponding to the set of targets (e.g., associated with one or more gut-related conditions, etc.), where the set of taxa includes at least one of: *Alistipes* (genus), *Barnesiella* (genus), *Bifidobacterium* (genus), *Campylobacter* (genus), *Peptoclostridium* (genus), *Escherichia-Shigella* (genus), *Fusobacterium* (genus), *Lactobacillus* (genus), *Odoribacter* (genus), *Prevotella* (genus), *Pseudoflavonifractor* (genus), *Roseburia* (genus), *Ruminococcus* (genus), *Salmonella* (genus), *Veillonella* (genus), *Akkermansia muciniphila* (species), *Anaerotruncus colihominis* (species), *Bacteroides fragilis* (species), *Bacteroides vulgatus* (species), *Bifidobacterium longum* (species), *Butyrivibrio crossotus* (species), *Campylobacter jejuni* (species), *Campylobacter coli* (species), *Campylobacter lari* (species), *Peptoclostridium difficile* (species), *Collinsella aerofaciens* (species), *Coprococcus eutactus* (species), *Desulfovibrio piger* (species), *Dialister invisus* (species), *Escherichia coli* (species), *Escherichia coli* O157 (species), *Faecalibacterium prausnitzii* (species), *Methanobrevibacter smithii* (species), *Oxalobacter formigenes* (species), *Ruminococcus albus* (species), *Ruminococcus bromii* (species), *Ruminococcus gnavus* (species), *Salmonella enterica* (species), *Salmonella bongori* (species), *Shigella boydii* (species), *Shigella sonnei* (species), *Shigella flexneri* (species), *Shigella dysenteriae* (species), *Streptococcus sanguinis* (species), *Streptococcus thermophilus* (species), *Vibrio cholerae* (species), *Yersinia enterocolitica* (species), *Alloprevotella* (genus), *Anaerofilum* (genus), *Bacteroides* (genus), *Blautia* (genus), *Butyricimonas* (genus), *Catenibacterium* (genus), *Christensenella* (genus), *Collinsella* (genus), *Coprococcus* (genus), *Dialister* (genus), *Eggerthella* (genus), *Faecalibacterium* (genus), *Flavonifractor* (genus), *Gelria* (genus), *Haemophilus* (genus), *Holdemania* (genus), *Oscillibacter* (genus), *Oscillospira* (genus), *Parabacteroides* (genus), *Paraprevotella* (genus), *Phascolarctobacterium* (genus), *Streptococcus* (genus), *Turicibacter* (genus), *Tyzzerella* (genus), *Acetobacter nitrogenifigens* (species), *Acinetobacter baumannii* (species), *Azospirillum brasilense* (species), *Bacillus cereus* (species), *Bacillus coagulans* (species), *Bacillus licheniformis* (species), *Bifidobacterium animalis* (species), *Bifidobacterium bifidum* (species), *Brevibacillus laterosporus* (species), *Christensenella minuta* (species), *Clavibacter michiganensis* (species), *Clostridium butyricum* (species), *Enterococcus italicus* (species), *Fibrobacter succinogenes* (species), *Kocuria rhizophila* (species), *Lactobacillus brevis* (species), *Lactobacillus coryniformis* (species), *Lactobacillus delbrueckii* (species), *Lactobacillus fermentum* (species), *Lactobacillus helveticus* (species), *Lactobacillus kefiranofaciens* (species), *Lactobacillus kunkeei* (species), *Lactobacillus rhamnosus* (species), *Lactobacillus salivarius* (species), *Lactococcus fujiensis* (species), *Lactococcus garvieae* (species), *Lactococcus lactis* (species), *Leptotrichia hofsta-*

*dii* (species), *Leuconostoc fallax* (species), *Leuconostoc kimchii* (species), *Oenococcus oeni* (species), *Paenibacillus apiarius* (species), *Pediococcus pentosaceus* (species), *Propionibacterium freudenreichii* (species), *Pseudoclavibacter helvolus* (species), *Renibacterium salmoninarum* (species), *Ruminococcus flavefaciens* (species), *Staphylococcus sciuri* (species), *Weissella koreensis* (species), *Clostridium* (genus), and *Clostridium difficile* (species). Additionally or alternatively, determining characterizations can be for any suitable microorganism-related taxa associated with any suitable targets. Regarding Block S150, performing the characterization process can be configured as measuring at least one of the following: a severity score, a presence metric, an absence metric, a risk score, and/or a significance index to associate a taxon or a set of taxa with a condition (or group of conditions) of interest in any manner analogous to that described in U.S. Provisional Application Ser. No. 62/558,489 filed 14 Sep. 2017, which is herein incorporated in its entirety by this reference.

Determining microbiome-associated characterizations is preferably based on microbiome datasets (e.g., microbiome features extracted from microbiome datasets; microbiome composition diversity features; microbiome functional diversity features; etc.). In variations, determining microbiome-associated characterizations can be based on at least one of: presence of microbiome features extracted from the microorganism sequence dataset, absence of the microbiome features, relative abundance for taxonomic groups of the set of taxa, diversity of microbiome composition features of the microbiome features, diversity of microbiome functional features of the microbiome features, a ratio between at least two features of the microbiome features associated with the set of taxa, interactions between the set of taxa, and phylogenetic distance between the set of taxa. Additionally or alternatively, determining microbiome-related characterizations can be based on at least one of: relative abundance comparisons; thresholds, weights, machine learning models, computer-implemented rules, and/or any other suitable aspects.

In variations, Block S150 and/or other suitable portions of the method 100 can include applying (e.g., generating, training, executing, updating, etc.) one or more models (e.g., microbiome characterization models; therapy models; gRNA-associated molecule selection models; etc.) including one or more of: probabilistic properties, heuristic properties, deterministic properties, and/or any other suitable properties. In an example, the method 100 can include: processing biological samples from a population of subjects with gRNA complexes (e.g., as in Block S120); receiving a supplementary dataset, associated with at least a subset of the population of subjects, where the supplementary dataset is informative of the microorganism-related condition (e.g., digital survey responses indicative of subjects exhibiting the microorganism-related condition; etc.); and transforming the supplementary dataset and features extracted from the at least one of the microbiome composition diversity dataset and the microbiome functional diversity dataset into a characterization model for the microorganism-related condition (e.g., a characterization model for determining characterizations; etc.). The method 100 can further include: collecting a user biological sample from a user, where the user biological sample includes a set of user targets sharing target sequences with the set of targets; sequencing the set of user targets based on at least one of: user-associated gRNA complexes sharing sequences with the proteins and the gRNAs, user-associated adapters sharing the adapter sequence, and user-associated primers sharing the primer sequence; generating a user microbiome dataset based on the sequenced set of user targets; and determining a microbiome-associated characterization for the user for the microorganism-related condition based on the user microbiome dataset and a characterization model. Each model can be run or updated: once; at a predetermined frequency; every time an instance of an embodiment of the method and/or sub-process is performed; every time a trigger condition is satisfied, and/or at any other suitable time frequency. The models can be run or updated concurrently with one or more other models, serially, at varying frequencies, and/or at any other suitable time. Each model can be validated, verified, reinforced, calibrated, or otherwise updated based on newly received, up-to-date data; historical data or be updated based on any other suitable data.

Determined microbiome-associated characterizations (and/or therapy models, and/or other suitable data, etc.) can be used for promoting therapies to users (e.g., users with the microorganism-related condition; at risk of the microorganism-related condition; etc.), where the therapy can modulate user microbiome composition to improve a state of the microorganism-related condition. Additionally or alternatively, promoting therapies to users can be performed in any suitable manner analogous to that described in U.S. application Ser. No. 15/707,907 filed 18 Sep. 2017, which is herein incorporated in its entirety by this reference. However, performing a characterization process and/or promoting therapies can be performed in any suitable manner.

In specific applications, the method 100 can be applied to generation of diagnostic tests that are based on sample processing, target amplification, and sequencing in an efficient manner. In specific applications, the diagnostic tests can be associated with at least one or more neurological health conditions, one or more autoimmune condition, one or more endocrine system conditions, one or more mental health conditions, one or more locomotor system conditions, one or more metabolic (associated) disease conditions, one or more cardiovascular disease conditions, one or more cutaneous conditions, one or more sexually transmitted diseases, one or more dental health conditions, one or more gastrointestinal health conditions, and/or any other suitable condition, embodiments, variations, and examples of which are described in U.S. application Ser. No. 14/919,614 filed on 21 Oct. 2015, U.S. application Ser. No. 15/097,862 filed on 13 Apr. 2016, U.S. application Ser. No. 15/098,027 filed on 13 Apr. 2016, U.S. application Ser. No. 15/098,248 filed on 13 Apr. 2016, U.S. application Ser. No. 15/098,236 filed on 13 Apr. 2016, U.S. application Ser. No. 15/098,222 filed on 13 Apr. 2016, U.S. application Ser. No. 15/098,204 filed on 13 Apr. 2016, U.S. application Ser. No. 15/098,174 filed on 13 Apr. 2016, U.S. application Ser. No. 15/098,110 filed on 13 Apr. 2016, U.S. application Ser. No. 15/098,081 filed on 13 Apr. 2016, and U.S. application Ser. No. 15/098,153 filed on 13 Apr. 2016, which are herein incorporated in their entireties by this reference.

The method 100 can additionally or alternatively include any other suitable blocks or steps configured to facilitate CRISPR-targeted sequencing applications. For instance, some variations of the method 100 can include automatically generating gRNAs of the method 100 within a laboratory environment including a robotic subsystem, such that the gRNAs can be directly applied to amplification of a set of targets of a sample acquired in Block S101 above. In specific examples, the robotic system can be one or more of: a Thermo Fischer Scientific™ robotic lab automation system, an Anton-Paar™ robotic lab automation system, a Transcriptic™ robotic lab automation system, a BioNex™ robotic lab automation system, a Hudson Robotics™ robotic lab automation system, a Biomek® laboratory automation workstation, and any other suitable robotic system that takes gRNA assembly materials (e.g., bases, oligonucleotide components, buffers, etc.) and assembles gRNAs of the set of gRNAs in solution, with a desired concentration and distribution of different gRNAs of the gRNA set. However, the method 100 can additionally or alternatively include any other suitable Blocks or Steps configured to design and/or apply a set of CRISPR materials for amplification and analysis of a set of targets.

In a specific example, the method 100 can include: extracting DNA from gut samples, such as using approaches described in U.S. application Ser. No. 15/707,907 filed 18 Sep. 2017, which is herein incorporated in its entirety by this reference; complexing spCas9 enzyme with gRNAs targeting the 16S region of bacteria to generate a ribonucleoprotein complex (RNP), which is incubated at 37 C (and/or other suitable temperatures) with the extracted DNA to allow complete digestion of target DNA; following sample clean-up and size selection, ligating adaptors onto the digested 16S fragments; performing PCR with indexing primers and sequences to bind to the adaptors; and sequencing bacterial 16S library on a sequencing system (e.g., the Illumina NextSeq platform in order to generate a microbiome dataset that can be used for determining characterizations, promoting therapies, and/or performing any other suitable processes.

The method 100 and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which includes one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Although omitted for conciseness, the embodiments include every combination and permutation of the various system components and the various method processes, including any variations, examples, and specific examples, where the method processes can be performed in any suitable order, sequentially or concurrently using any suitable system components.

As a person skilled in the art will recognize from the previous detailed description and from the figures and claims, modifications and changes can be made to the embodiments of the invention without departing from the scope of this invention as defined in the following claims.

We claim:

1. A method of obtaining a sequenced set of target for generating at least one of a microbiome composition diversity dataset and a microbiome functional diversity dataset, the method comprising:

generating guide RNA (gRNA) complexes comprising proteins and gRNAs of a set of targets corresponding to a set of taxa associated with a microorganism-related condition, each of the set of targets comprising an internally transcribed spacer (ITS) sequence for fungal identification, at least one of a 16S rRNA sequence for prokaryotic identification, and an 18S rRNA sequence for eukaryotic identification, wherein the proteins of the gRNA complexes comprise endonucleases for generating microorganism nucleic acid fragments comprising a set of blunt end regions associated with the set of targets;

processing microorganism nucleic acid material with the gRNA complexes to generate end regions associated with the set of targets, wherein processing the microorganism nucleic acid material comprises processing samples from a population of subjects with the gRNA complexes, each of the samples comprising a plurality of microorganism targets;

obtaining ligated end regions by ligating the end regions with a set of adapters sharing a same adapter sequence;

obtaining an amplified set of targets by simultaneously amplifying the set of targets based on the ligated end regions and a set of primers sharing a same primer sequence in order to facilitate reduced amplification bias, wherein the shared primer sequence is associated with the shared adapter sequence; and obtaining the sequenced set of targets by performing sequencing on the amplified set of targets associated with the reduced amplification bias.

2. The method of treating a microorganism-related condition, the method comprising:

generating the sequenced set of targets with reduced amplification bias in accordance with the method of claim 1;

generating at least one of a microbiome composition diversity dataset and a microbiome functional diversity dataset based on the sequenced set of targets;

receiving a supplementary dataset, associated with at least a subset of the population of subjects, wherein the supplementary dataset is informative of the microorganism-related condition;

transforming the supplementary dataset and features extracted from the at least one of the microbiome composition diversity dataset and the microbiome functional diversity dataset into a characterization model for the microorganism-related condition;

collecting a user sample from a user, wherein the user sample comprises user sample nucleic acid material sharing target sequences with the set of targets;

generating a user microbiome dataset by sequencing the user sample nucleic acid material based on user-associated gRNA complexes sharing sequences with the proteins and the gRNAs, user-associated adapters sharing the adapter sequence, and user-associated primers sharing the primer sequence;

determining a microbiome-associated characterization for the user for the microorganism-related condition based on the user microbiome dataset and the characterization model; and providing a therapy to the user with the microorganism-related condition based on the microbiome-associated characterization and a therapy model, wherein the therapy modulates user microbiome composition to improve a state of the microorganism-related condition.

3. The method of claim 2, wherein the set of targets corresponding to the set of taxa comprises a plurality of targets associated with at least one of: *Alistipes* (genus), *Barnesiella* (genus), *Bifidobacterium* (genus), *Campylobacter* (genus), *Peptoclostridium* (genus), *Escherichia-Shigella* (genus), *Fusobacterium* (genus), *Lactobacillus* (genus), *Odoribacter* (genus), *Prevotella* (genus), *Pseudoflavonifractor* (genus), *Roseburia* (genus), *Ruminococcus* (genus), *Salmonella* (genus), *Veillonella* (genus), *Akkermansia muciniphila* (species), *Anaerotruncus colihominis* (species), *Bacteroides fragilis* (species), *Bacteroides vulgatus* (species), *Bifidobacterium longum* (species), *Butyrivibrio crossotus* (species), *Campylobacter jejuni* (species), *Campylobacter coli* (species), *Campylobacter lari* (species), *Peptoclostridium difficile* (species), *Collinsella aerofaciens* (species), *Coprococcus eutactus* (species), *Desulfovibrio piger* (species), *Dialister invisus* (species), *Escherichia coli* (species), *Escherichia coli* O157 (species), *Faecalibacterium prausnitzii* (species), *Methanobrevibacter smithii* (species), *Oxalobacter formigenes* (species), *Ruminococcus albus* (species), *Ruminococcus bromii* (species), *Ruminococcus gnavus* (species), *Salmonella enterica* (species), *Salmonella bongori* (species), *Shigella boydii* (species), *Shigella sonnei* (species), *Shigella flexneri* (species), *Shigella dysenteriae* (species), *Streptococcus sanguinis* (species), *Streptococcus thermophilus* (species), *Vibrio cholerae* (species), and *Yersinia enterocolitica* (species).

4. The method of claim 2, wherein the set of taxa corresponding to the set of targets comprises at least one of: *Actinomyces* (genus), *Aerococcus* (genus), *Alloiococcus* (genus), *Anaerococcus* (genus), *Anaeroglobus* (genus), *Anaerostipes* (genus), *Anaerotruncus* (genus), *Arcanobacterium* (genus), *Arthrospira* (genus), *Atopobium* (genus), *Bacteroides* (genus), *Bulleidia* (genus), *Campylobacter* (genus), *Catenibacterium* (genus), Coriobacteriaceae (family), *Corynebacterium* (genus), *Dialister* (genus), *Eggerthella* (genus), *Enterococcus* (genus), *Escherichia* (genus), *Finegoldia* (genus), *Fusobacterium* (genus), *Gardnerella* (genus), *Gemella* (genus), Lactobacillaceae (family), Lactobacillales (order), *Lactobacillus* (genus), *Leptotrichia* (genus), *Megasphaera* (genus), *Mobiluncus* (genus), *Moryella* (genus), *Mycoplasma* (genus), *Papillibacter* (genus), *Parvimonas* (genus), *Peptococcus* (genus), *Peptoniphilus* (genus), *Peptostreptococcus* (genus), Porphyromonadaceae (family), *Porphyromonas* (genus), *Prevotella* (genus), Prevotellaceae (family), *Pseudomonas* (genus), *Ruminococcus* (genus), *Segniliparus* (genus), *Shigella* (genus), *Sneathia* (genus), *Staphylococcus* (genus), *Streptococcus* (genus), *Treponema* (genus), *Ureaplasma* (genus), *Veillonella* (genus), Veillonellaceae (family), *Aerococcus christensenii* (species), *Aerococcus* spp. (genus), *Algoriphagus aquatilis* (species), *Anaerococcus* spp. (genus), *Anaerococcus tetradius* (species), *Anaerococcus vaginalis* (species), *Anoxybacillus pushchinoensis* (species), *Atopobium* spp. (genus), *Atopobium vaginae* (species), *Bacteroides fragilis* (species), *Bacteroides* spp. (genus), *Bifidobacterium animalis* subsp. *lactis* (species), *Bifidobacterium dentium* (species), *Bifidobacterium lactis* (species), *Bifidobacterium iongum* subsp. *suis* (species), *Bulleidia extructa* (species), *Burkholderia fungorum* (species), *Burkholderia phenoliruptrix* (species), *Caldicellulosiruptor saccharolyticus* (species), *Campylobacter* spp. (genus), *Campylobacter ureolyticus* (species), *Candida albicans* (species), *Candida glabrata* (species), *Candida krusei* (species), *Candida lusitaniae* (species), *Candidatus Mycoplasma girerdii* (species), *Catenibacterium* spp. (genus), *Chlamydia trachomatis* (species), *Chondromyces robustus* (species), *Clostridiales* BVAB2 (species), *Clostridiales* BVAB3 (species), *Clostridium cavendishii* (species), *Clostridium viride* (species), *Cryobacterium psychrophilum* (species), *Dialister micraerophilus* (species), *Dickeya chrysanthemi* (species), *Eggerthia catenaformis* (species), *Erwinia chrysanthemi* (species), *Escherichia coli* (species), *Escherichia fergusonii* (species), *Exiguobacterium acetylicum* (species), *Fusobacterium nucleatum* (species), *Fusobacterium* spp. (genus), *Gardnerella* spp. (genus), *Gardnerella vaginalis* (species), *Gemella* sp. (genus), *Haemophilus ducreyi* (species), *Klebsiella granulomatis* (species), Lachnospiraceae BVAB1 (species), *Lactobacillus acidophilus* (species), *Lactobacillus brevis* (species), *Lactobacillus casei* (species), *Lactobacillus casei Shirota* (species), *Lactobacillus crispatus* (species), *Lactobacillus delbrueckii* (species), *Lactobacillus fermentum* (species), *Lactobacillus gasseri* (species), *Lactobacillus iners* (species), *Lactobacillus jensenii* (species), *Lactobacillus johnsonii* (species), *Lactobacillus kefiranofaciens* (species), *Lactobacillus paracasei* $FJ86_{1111.1}$ (species), *Lactobacillus pentosus* strain S-PT84 (species), *Lactobacillus plantarum* (species), *Lactobacillus reuteri* (species), *Lactobacillus reuteri* RC-14 (species), *Lactobacillus rhamnosus* (species), *Lactobacillus rhamnosus* (strain BMX 54) (species), *Lactobacillus rhamnosus* BMX 54 (species), *Lactobacillus rhamnosus* GR-1 (species), *Lactobacillus salivarius* (species), *Lactobacillus vaginalis* (species), *Leptotrichia* spp. (genus), *Maribacter orientalis* (species), *Megasphaera genomosp* (species), *Megasphaera micronuciformis* (species), *Megasphaera* spp. (genus), *Microbacterium halophilum* (species), *Mobiluncus curtisii* (species), *Mobiluncus mulieris* (species), *Moorella glycerini* (species), *Mycoplasma genitalium* (species), *Mycoplasma hominis* (species), *Mycoplasma muris* (species), *Neisseria gonorrhoeae* (species), *Paeniclostridium sordellii* (species), *Papillibacter* spp. (genus), *Parastreptomyces abscessus* (species), *Parvimonas micra* (species), *Parvimonas* spp. (genus), *Pasteurella multocida* (species), *Pediococcus ethanolidurans* (species), *Peptoniphilus harei* (species), *Peptoniphilus indolicus* (species), *Peptoniphilus* spp. (genus), *Peptostreptococcus anaerobius* (species), *Peptostreptococcus massiliae* (species), *Peptostreptococcus* spp. (genus), *Porphyromonas gingivalis* (species), *Porphyromonas levii* (species), *Porphyromonas* sp. (genus), *Porphyromonas uenonis* (species), *Prevotella amnii* (species), *Prevotella bivia* (species), *Prevotella disiens* (species), *Prevotella intermedia* (species), *Prevotella oralis* (species), *Prevotella oris* (species), *Prevotella timonensis* (species), *Pseudomonas* spp. (genus), *Ralstonia pickettii* (species), *Ruminococcus* spp. (genus), *Sanguibacter keddieii* (species), *Sneathia amnii* (species),

*Sneathia sanguinegens* (species), *Sneathia* spp. (genus), *Staphylococcus aureus* (species), *Staphylococcus mulans* (species), *Staphylococcus pasteuri* (species), *Staphylococcus simiae* (species), *Staphylococcus simulans* (species), *Staphylococcus* spp. (genus), *Staphylococcus warneri* (species), *Streptococcus agalactiae* (species), *Streptococcus anginosus* (species), *Streptococcus intermedius* (species), *Streptococcus pyogenes* (species), *Streptococcus viridans* (species), *Thermosipho atlanticus* (species), *Thermovirga lienii* (species), *Treponema pallidum* (species), *Trichomonas vaginalis* (species), *Trueperella bernardiae* (species), *Ureaplasma parvum* (species), *Ureaplasma urealyticum* (species), *Veillonella montpellierensis* (species), *Veillonella parvula* (species), *Virgibacillus proomii* (species), *Zobellia laminariae* (species), HPV 3 (virus variant), HPV 6 (virus variant), HPV 16 (virus variant), HPV 18 (virus variant), HPV 31 (virus variant), HPV 33 (virus variant), HPV 35 (virus variant), HPV 39 (virus variant), HPV 43 (virus variant), HPV 45 (virus variant), HPV 51 (virus variant), HPV 52 (virus variant) HPV 53 (virus variant), HPV 54 (virus variant), HPV 56 (virus variant), HPV 58 (virus variant), HPV 59 (virus variant), HPV 66 (virus variant), HPV 68 (virus variant), HPV (virus), and HPV (multiple type) (virus).

5. The method of claim 2, wherein the microorganism-related condition comprises a gut-related condition comprising at least one of: diarrhea, irritable bowel syndrome (IBS), inflammatory bowel disease (IBD), Crohn's Disease, ulcerative colitis, constipation, abdominal tenderness, bloating, flatulence, obesity, type II diabetes, prediabetes, kidney stones, cardiovascular health, and anxiety.

6. The method of claim 1, wherein generating the gRNA complexes comprises selecting gRNA sequences based upon at least one of: a folding energy factor, a hybridization factor, a GC content factor, a nucleotide run factor; a first binding energy factor, a second binding energy factor, and a GC clamp factor.

7. The method of claim 6, wherein ligating the end regions comprises ligating the set of blunt end regions with the set of adapters sharing the adapter sequence.

8. The method of claim 1, wherein the set of adapters sharing the adapter sequence facilitates next generation sequencing with a next generation sequencing platform, and wherein performing sequencing of the set of targets comprises performing next generation sequencing with the next generation sequencing platform based on the set of primers and the set of adapters.

9. The method of claim 1, wherein the proteins of the gRNA complexes are associated with protein type families comprising at least one of: cas, cpf, cas, cse, csy, csn, csd, cst, csh, csa, csm, and cmr.

10. The method of claim 9, wherein the proteins of the gRNA complexes are associated with protein types comprising at least one of: Cas9 and Cpf1.

11. The method of claim 1, wherein processing the microorganism nucleic acid material with the gRNA complexes to generate the end regions comprises:
processing the microorganism nucleic acid material with the gRNA complexes to generate sticky end regions associated with the set of targets; and
processing the sticky end regions to generate blunt end regions associated with the set of targets, wherein ligating the end regions with the set of adapters sharing the adapter sequence comprises ligating the blunt end regions with the set of adapters.

\* \* \* \* \*